United States Patent [19]
Klein et al.

[11] Patent Number: 5,468,769
[45] Date of Patent: Nov. 21, 1995

[54] PACLITAXEL DERIVATIVES

[75] Inventors: Larry L. Klein, Lake Forest; Clarence J. Maring, Grayslake, both of Ill.

[73] Assignee: Abbott Laboratories, Abbott Park, Ill.

[21] Appl. No.: 92,124

[22] Filed: Jul. 15, 1993

[51] Int. Cl.[6] .................... A61K 31/335; C07D 305/14
[52] U.S. Cl. ................ 514/449; 549/510; 549/511
[58] Field of Search .................... 549/510, 511; 514/449

[56] References Cited

U.S. PATENT DOCUMENTS

| | | | |
|---|---|---|---|
| 4,942,184 | 7/1990 | Haugwitz et al. | 514/449 |
| 5,352,806 | 10/1994 | Gunawardana et al. | 549/510 |

*Primary Examiner*—C. Warren Ivy
*Assistant Examiner*—Ba K. Trinh
*Attorney, Agent, or Firm*—Andreas M. Danckers

[57] ABSTRACT

A compound or prodrug thereof having the formula

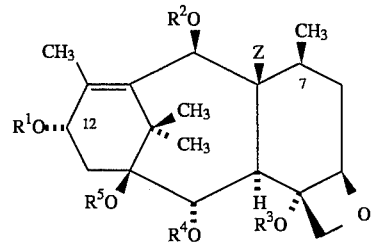

wherein —$OR^1$ comprises the C-13 side-chain of taxol and Z is selected from the group consisting of —CHO, —$CH_2OH$, —$CH_2OR'$, —$CH_2NR'R''$, —CH=NR', —CH=NOR', —CH=NNR=R'', —CH(OH)$SO_3$Na, —$CH_2OPO_3^=$, —$CH_2OSO_3^=$, —CN and a radical of the formula

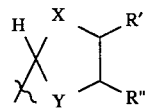

where X and Y are independently selected from —O—, —S—, and —N(R')—, as well as a method for preparing the compounds of the invention, a method of their use for the inhibition of tumors and pharmaceutical compositions containing the same.

8 Claims, 1 Drawing Sheet

PACLITAXEL DERIVATIVES

BACKGROUND OF THE INVENTION

The present invention relates to plant-derived chemotherapeutic compounds. More particularly, the invention is directed to ring-contracted taxane compounds and especially rearrangement products related to a naturally occurring compound isolated from *Taxus canadensis*, as well as novel analogs of parlitaxel prepared therefrom.

Paclitaxel, a member of the taxane family of terpenes, is of interest as a chemotherapeutic agent against a broad range of cancers. Paclitaxel has been shown to be effective against advanced breast and ovarian cancers in clinical trials and has exhibited promising activity against a number of other tumor types in preliminary investigations. A summary of the current state of paclitaxel research, development and clinical testing may be found in Borman, Chem/ca/& Eng/neering News (Sep. 2, 1991), 11–18; a review of synthetic efforts in the paclitaxel field is provided by D. G. I. Kingston in Pharm. 7her. 52:1 (1991).

Paclitaxel, which possesses the structural formula

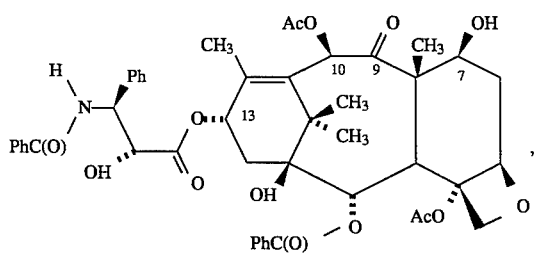

is currently limited in supply, as it is obtained primarily by extraction from the bark and, to a lesser amount, the leaves of trees and bushes of the genus Taxus. The primary source of paclitaxel, the Pacific yew *Taxus brevifolia*, is a slow-growing evergreen with limited geographic distribution and increasing scarcity. Furthermore, the isolation of paclitaxel, which constitutes less than 400 parts per million of the tree bark, is a difficult, low-yield and expensive process. Neither long-term nor large-scale harvesting of yews is considered an acceptable option for ecological as well as commercial reasons. There is, consequently, a pressing need for additional supplies of taxol for clinical use and testing.

While the needles of other Taxus species are being explored as renewable sources of paclitaxel and its precursors, some researchers have attempted to produce paclitaxel in tissue and cell culture. Total chemical synthesis of the compound and its related analogs has been attempted but not yet been achieved. The chemical conversion of naturally occurring paclitaxel precursors such as baccatin III and cephalomannine to paclitaxel itself or its analogs has been reported; however, additional routes for production of potentially active taxanes and related compounds are still needed.

Paclitaxel prodrugs or derivatives having greater water solubility than the naturally-occurring taxols have also been sought. The ability to synthesize ring-contracted compounds having potentially superior pharmacological properties may offer significant advantages to the chemist and pharmacologist. It is therefore an object of the present invention to provide such compounds and the means for their preparation.

SUMMARY OF THE INVENTION

In one aspect of the present invention is disclosed the ring-contracted compound (resulting from the rearrangement of 13-acetyl-9-dihydrobaccatin III) having the following structural formula (I):

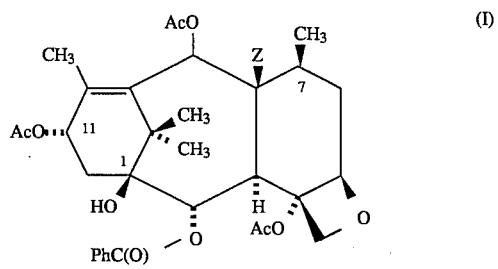

or a prodrug thereof.

In formula (i), "Ph" and "Ac" represent phenyl and zcetyl radicals, respectively, and Z is selected from —CHO, —CH$_2$OH, —CH$_2$OR', —CH$_2$NR'R", —CH=NR', —CH=NOR', —CH=NNR'R", —CH(OH)SO$_3$Na, —CH$_2$OPO$_3^3$, —CH$_2$OSO$_3^=$,

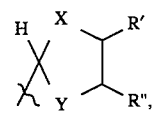

—CN and a radical of the formula where X and Y are independently selected from —O—, —S— and —N(R')—, and R' and R" are independently selected at each occurrence from hydrogen, alkyl, alkanoyl and aminoalkanoyl.

In another, more general aspect of the invention are disclosed taxane analogs having the structural formula (II);

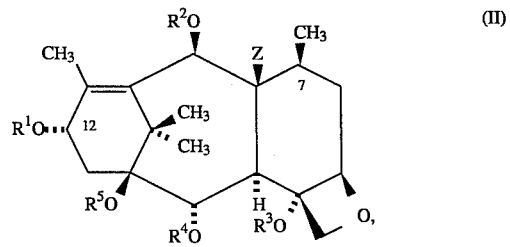

and the respective prodrugs thereof. In formula (II), Z is as previously described while R$^1$ is selected from hydrogen, alkanoyl and a radical of the formula

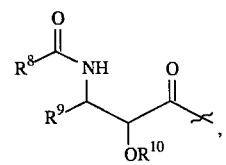

in which R$^8$ is hydrogen, alkyl, phenyl, substituted phenyl, alkoxy, substituted alkoxy, amino, substituted amino, phenoxy or substituted phenoxy; R$^9$ is hydrogen, alkyl, hydroxyalkyl, alkoxyalkyl, aminoalkyl, phenyl, substituted phenyl, α-naphthyl, β-naphthyl or heteroaryl; and R10 is hydrogen, alkanoyl, substituted alkanoyl or aminoalkanoyl R$^2$, R$^3$ and R$^5$ in formula (11) are independently selected from hydrogen, alkyl, alkanoyl and aminoalkanoyl.

R$^4$ in formula (II)is hydrogen, alkyl, alkanoyl, aminoalkanoyl or phenylcarbonyl (—C(O)—phenyl).

It is expected that these compounds will be useful in connection with the treatment, or in the preparation of paclitaxel derivatives for use in the treatment, of cancers and leukemias. It is also expected that appropriate substitutions in the 8-position as shown will lead to improvements in the water solubility of these compounds.

In further aspects of the present invention are disclosed tumor-inhibiting pharmaceutical compositions comprising a pharmaceutically acceptable carrier and a compound of the invention, as well as a method of inhibiting tumors in a mammal in need of such treatment comprising administering to the mammal a therapeutically effective amount of a compound of the invention.

BRIEF DESCRIPTION OF THE DRAWING

The present invention is disclosed in connection with the appended drawing, in which.

DETAILED DESCRIPTION OF THE INVENTION

Figure 1:
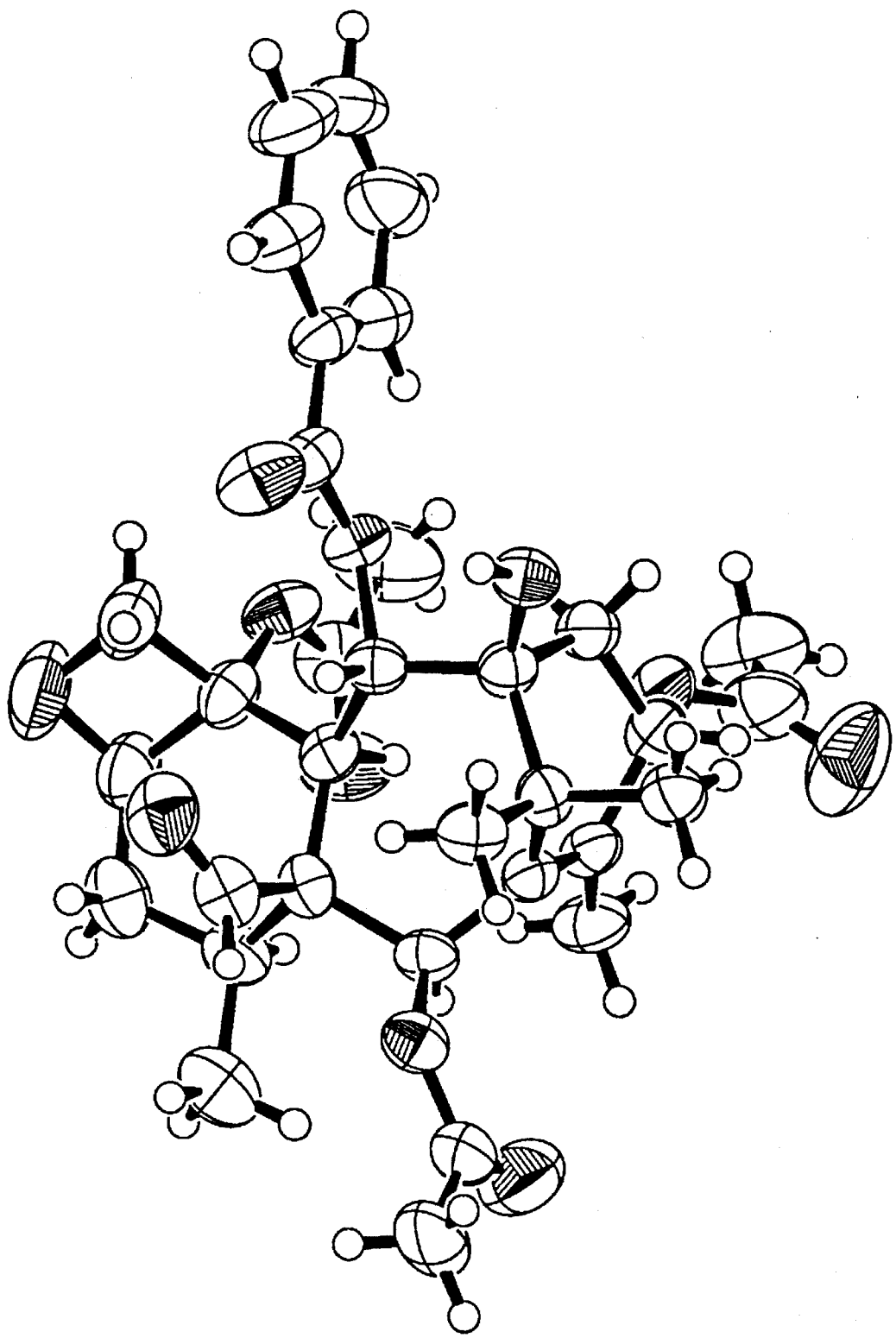
FIG. 1 is a depiction of the 3-dimensional structure of 4,9,12-tris(acetyloxy)-2-benzoyloxy- 8-formyl-1,2,3,4,5,6,7,8,10,13,14-undecahydro-1-hydroxy-7,14,14,17-tetramethyl- 1,10-methano-20H-cyclonona[2,3]benz[1,2-b]oxete (the compound of formula (I) where Z is —CHO).

The present invention comprises the 9-dihydro-13-acetylbaccatin III ring-contracted compound of formula (I), as well as derivatives thereof having the structural formula (11) wherein groups Z, $R^1$ through $R^{10}$, R' and R" are as described above. Included among the compounds of the invention are those wherein —$OR^1$ is the C-13 side-chain of paclitaxel or a radical having the formula

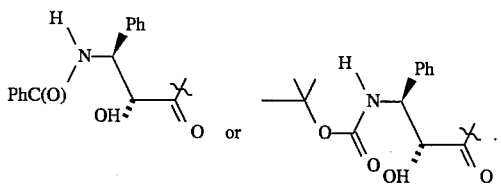

The following definitions apply to these compounds and throughout the present disclosure:

The term "alkyl" as used herein refers to a monovalent group derived by the removal of a single hydrogen atom from a straight- or branched-chain saturated hydrocarbon containing one to six carbon atoms including, but not limited to, methyl, ethyl, n- and iso-propyl, n-, sec-, iso- and tert-butyl, pentyl and hexyl.

The term "alkanoyl" as used herein refers to an alkyl function as defined above attached via a carbonyl group including, but not limited to, acetyl, propionyl, butanoyl and isobutanoyl.

The term "alkoxy' as used herein refers to an alkyl function as defined above attached via an oxygen atom including, but not limited to, methoxy, ethoxy, isopropoxy, butoxy and tert-butoxy.

The term "aminoalkanoyl" as used herein refers to an alkanoyl function as defined above substituted with between one and three amino groups including, but not limited to, 2-aminopropanoyl, 4-aminobutanoyl and 6-aminohexanoyl. Additionally, the amino groups may optionally be substituted with peptidyl residues of the naturally occurring amino acids, as well as di- and tripeptide residues formed therefrom.

The term "aminoalkyl" as used herein refers to an alkyl function as defined above substituted with amino or substituted amino, as defined elsewhere herein.

The term "halogen" as used herein refers to a group selected from bromo (Br), chloro (Cl), fluoro (F) and iodo (I).

The term "haloalkyl" as used herein refers to an alkyl group as defined above substituted with between one and three halogen atoms including, but not limited to, fluoromethyl, trifluoromethyl and fluoroethyl.

The terms "heteroaryl" or "heterocyclic aromatic" as used herein refer to 5and 6-membered aromatic rings having in the ring one, two or three heteroatoms selected from N, O and S; and also including benzo fused analogs of these 5- and 6-membered heterocyclic aromatic rings including, but not limited to, pyridyl, quinolyl, isoquinolyl, quinazolinyl, phthalazinyl, quinoxalinyl, furyl, imidazolyl, benzofuryl, benzothienyl, pyrrolyl, thienyl, thiazolyl, isothiazolyl, isoxazolyl, pyrazolyl, pyrazinyl, pyridazinyl, pyrimidyl, indolyl and the like.

The terms "N-protected" and "N-protecting" as used herein refer to the use of a group intended to protect an amino function or the N-terminus of an amino acid or peptide against undesirable reactions during a synthetic procedure or to prevent the attack of exopeptidases on the compound or to increase the solubility of the compound and includes, but is not limited to, such uses of sulfonyl; acyl, such as acetyl, pivaloyl and benzoyl; alkoxycarbonyl, such as tert-butyloxycarbonyl (BOC), benzyloxycarbonyl (Cbz); and L- or D-aminoacyl residues, which may themselves be N-protected. Other examples may be found in The Peptides, E. Gross and J. Meienhofer, Vol. 3, Academic Press (1981), incorporated herein by reference.

The term "prodrug" as used herein refers to compounds that are rapidly transformed in vivo to yield the parent compounds of formulae (I) or (II), as for example by hydrolysis in blood. T. Higuchi and V. Stella provide a thorough discussion of the prodrug concept in "Prodrugs as Novel Delivery Systems", A. C. S. Symposium Series, Vol. 14, American Chemical Society (1975), incorporated herein by reference. Examples of esters useful as prodrugs for compounds containing carboxyl groups can be found on pages 14–21 of "Bioreversible Carriers in Drug Design: Theory and Application", ed. E. B. Roche, Pergamon Press (1987), incorporated herein by reference.

The term "prodrug ester group" as used herein refers to any of several esterforming groups that are hydrolyzed under physiological conditions. Examples of prodrug ester groups include pivaloyloxymethyl, acetoxymethyl, phthalidyl, indanyl and methoxymethyl, as well as other such groups known in the art.

The term "protecting group" as used herein is a term well-known in the art and refers to substituents on functional groups of compounds undergoing chemical transformation which prevent undesired reactions and degradations during a synthesis; see, for example, T. H. Greene, "Protective Groups in Organic Synthesis," John Wiley & Sons (1981), incorporated herein by reference.

The term "substituted alkanoyl" as used herein refers to an alkanoyl group as defined above substituted with between one and three groups independently selected from hydroxyl, sulfhydryl, alkoxyl, carboxyl and halogen.

The term "substituted alkoxy" as used herein refers to an alkoxy group as defined above substituted with between one and three groups independently selected from hydroxyl, sulfhydryl, alkoxyl, thioalkoxyl, carboxyl, amino and halogen.

The term "substituted amino" as used herein refers to an amino group substituted with one or two alkyl groups including, but not limited to, t-butylamino, benzylamino, and N,N-dimethylamino.

The term "substituted heteroaryl" as used herein refers to a heteroaryl group substituted with one or two substituents independently selected from hydroxy, halo, alkylimino (=NR$^{99}$, where R$^{99}$ is an alkyl group), amino, alkylamino, dialkylamino, alkoxy, polyalkoxy, haloalkyl, cycloalkyl, aryl, arylalkyl, —COOh, —SO$_3$H and loweralkyl; additionally, nitrogen-containing heterocycles can be N-protected as described above.

The term "substituted phenyl" as used herein refers to a phenyl group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and —OSO$_3$H.

The term "substituted phenoxy" as used herein refers to a phenoxy group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and —OSO$_3$H.

The term "thioalkoxy" as used herein refers to an alkoxy group as defined above wherein a sulfur atom is substituted for the oxygen atom.

Compounds falling within the scope of the present invention include the following:

4,9,12(Tris(acetyloxy)-2-benzoyloxy-8-formyl- 1,2,3,4,5,6,7,8,10,13,14-undecahydro-1-hydroxy-7,14,14,17 -tetramethyl- 1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy-8-hydroxymethyl- 7,14,14,17-tetramethyl- 1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy-8-methoxymethyl- 7,14,14,17-tetramethyl1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy-8-ethoxymethyl- 7,14,14,17-tetramethyl- 1,10-methano-20H-cyclonona[2,3]benz[1,2b]oxete;

4,9,12-Tris(acetyloxy)-8-acetyloxymethyl-2-benzoyloxy-1,2,3,4,5,6,7,8,10,13,14-undecahydro- 1-hydroxy-7,14,14,17-tetramethyl-1,10-methano-20H-cyclonona[2,3]benz[1,2-b]oxete;

4,9,12-Tris(acetyloxy)-2-benzoyloxy-8-dimethylaminomethyl-1,2,3,4,5,6,7,8,10,13,14-undecahydro- 1-hydroxy-7,14,14,17-tetramethyl-1,10-methano-20H-cyclonona[2,3]benz[1,2-b]oxete;

4,9,12-Tris(acetyloxy)-2-benzoyloxy-8-diethylaminomethyl-1,2,3,4,5,6,7,8,10,13,14-undecahydro- 1-hydroxy-7,14,14,17-tetramethyl-1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy- 7,14,14,17-tetramethyl-8-methylamino- 1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy-7,14,14,17-tetramethyl-8-ethylamino-1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy-7,14,14,17-tetramethyl-8-methylim ino-1,10-methano-20H-cyclonona[2,3]benz[1,2-b]oxete;

4,9,12-Tris(acetyloxy)-2-benzoyloxy-1,2,3,4,5,6,7,8,10,13,14-undecahydro- 1-hydroxy-7,14,14,17-tetramethyl-8-methoxyimino-1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy-7,14,14,17-tetramethyl-8-methylhydrazinomethyl-1,10-methano-20H-cyclonona[2,3]benz[1,2-b]oxete;

4,9,12-Tris(acetyloxy)-2-benzoyloxy-8-cyano-1,2,3,4,5,6,7,8,10,13,14-1-undecahydro-1-hydroxy- 7,14,14,17-tetramethyl-1,10-methano-20H-cyclonona[2,3]benz[1,2-b]oxete;

4,9,12-Tris(acetyloxy)-2-benzoyloxy-1,2,3,4,5,6,7,8,10,13,14-undecahydro-1-hydroxy-7,14,14,17-tetramethyl-1,10-methano-20H-cyclonona[2,3]benz[1,2b]oxete-8-methylsulfate;

4,9,12-Tris(acetyloxy)-2-benzoyloxy-1,2,3,4,5,6,7,8,10,13,14-undecahydro-1-hydroxy-7,14,14,17-tetramethyl-1,10-methano-20H-cyclonona[2,3]benz[1,2b]oxete-8-methylphosphate;

4,9,12-Tris(acetyloxy)-2-benzoyloxy-8-( 1,3-dioxolan-2-yl)-1,2,3,4,5,6,7,8,10,13,14-undecahydro- 1-hydroxy-7,14,14,17-tetramethyl-1,10-methano-20H-cyclonona[2,3]benz[1,2-b]oxete;

4,9,12-Tris(acetyloxy)-2-benzoyloxy-8-(tetrahydro-oxazole-2-yl)-1,2,3,4,5,6,7,8,10,13,14-undecahydro- 1-hydroxy-7,14,14,17-tetramethyl-1,10-methano-20H-cyclonona[2,3]benz[1,2-b]oxete;

4,9,12-Tris(acetyloxy)-2-benzoyloxy-8-( 1,3-dithiolane-2-yl)-1,2,3,4,5,6,7,8,10,13,14-undecahydro- 1-hydroxy-7,14,14,17-tetramethyl-1,10-methano-20H-cyclonona[2,3]benz[1,2-b]oxete;

4,9-Bis(acetyloxy)-2-benzoyloxy-8-formyl-1,12-dihydroxy-1,2,3,4,5,6,7,8,10,13,14-undecahydro- 7,14,14,17-tetramethyl-1,10-methano-20H-cyclonona[2,3]benz[1,2-b]oxete;

4,9-Bis(acetyloxy)-2-benzoyloxy-1,12-dihydroxy-1,2,3,4,5,6,7,8,10,13,14-undecahydro-8-hydroxymethyl- 7,14,14,17-tetramethyl-1,10-methano-2OH-cyclonona[2,3]benz[1,2-b]oxete;

4,9-Bis(acetyloxy)-2-benzoyloxy-1,12-dihydroxy-1,2,3,4,5,6,7,8,10,13,14-1undecahydro-8-methoxymethyl- 7,14,14,17-tetramethyl-1,10-methano-2OH-cyclonona[2,3]benz[1,2-b]oxete;

4,9-Bis(acetyloxy)-2-benzoyloxy-1,12-dihydroxy-1,2,3,4,5,6,7,8,10,13,14-undecahydro-8-ethoxymethyl- 7,14,14,17-tetramethyl-1,10-methano-2OH-cyclonona[2,3]benz[1,2-b]oxete;

4,9-Bis(acetyloxy)-8-acetyloxymethyl-2-benzoyloxy-1,12-dihydroxy-1,2,3,4,5,6,7,8,10,13,14-undecahydro- 7,14,14,17-tetramethyl-1,10-methano-2OH-cyclonona[2,3]benz[1,2-b]oxete;

4,9-Bis(acetyloxy)-2-benzoyloxy-8-dimethylaminomethyl-1,12-dihydroxy-1,2,3,4,5,6,7,8,10,13,14-undecahydro- 7,14,14,17-tetramethyl-1,10-methano-2OH-cyclonona[2,3]benz[1,2-b]oxete;

4,9-Bis(acetyloxy)-2-benzoyloxy-8-diethylaminomethyl-1,12-dihydroxy-1,2,3,4,5,6,7,8,10,13,14-undecahydro-7,14,14,17-tetramethyl-1,10-methano-2OH-cyclonona[2,3]benz[1,2-b]oxete;

4,9-Bis(acetyloxy)-2-benzoyloxy-1,12-dihydroxy-1,2,3, 4,5,6,7,8,10,13,14-1-undecahydro- 7,14,14,17-tetramethyl-8-methylamino-1,10-methano-2OH-cyclonona[2,3]benz[1,2-b]oxete;

4,9-Bis(acetyloxy)-2-benzoyloxy-1,12-dihydroxy-1,2,3,4,5,6,7,8,10,13,14-undecahydro-7,14,14,17-tetramethyl-8-ethylamino-1,10-methano-2OH-cyclonona[2,3]benz[1,2-b]oxete;

4,9-Bis(acetyloxy)-2-benzoyloxy-1,12-dihydroxy-1,2,3,4,5,6,7,8,10,13,14-undecahydro-7,14,14,17-tetramethyl-8-methylimino-1,10-methano-2OH-cyclonona[2,3]benz[1,2-b ]oxete;

4,9-Bis(acetyloxy)-2-benzoyloxy-1,12-dihydroxy-1,2,3,4,5,6,7,8,10,13,14-undecahydro-7,14,14,17-tetramethyl-8-methoxyimino-1,10-methano-2OH-cyclonona[2,3]benz[1,2-b]oxete;

4,9-Bis(acetyloxy)-2-benzoyloxy-1,12-dihydroxy-1,2,3,4,5,6, 7,8,10,13,14-undecahydro- 7,14,14,17-tetramethyl-8-methylhydrazinomethyl-1,10-methano-2OH-cyclonona[2,3]benz[1,2-b]oxete;

4,9-Bis(acetyloxy)-2-benzoyloxy-8-cyano-1,12-dihydroxy-1,2,3,4,5,6,7,8,10,13,14-undecahydro- 7,14,14,17-tetramethyl1,10-methano-2OH-cyclonona[2,3]benz[1,2-b]oxete;

4,9-Bis(acetyloxy)-2-benzoyloxy-1,12-dihydroxy-1,2,3,4,5,6,7,8,10,13,14-undecahydro-7,14,14,17-tetramethyl-1,10-methano-2OH-cyclonona[2,3]benz[1,2b ]oxete-8-methylsulfate;

4,9-Bis(acetyloxy)-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2b]oxete-8-methylphosphate;

4,9-Bis(acetyloxy)-2-benzoyloxy-8-(1,3-dioxolan-2-yl)-1,12-dihydroxy-1,2,3,4,5,6,7,8,10,13,14 -undecahydro-7,14,14,17-tetramethyl-1,10-methano-20H-cyclonona[2,3]benz[1,2-b]oxete;

4,9-Bis(acetyloxy)-2-benzoyloxy-8-(tetrahydro-oxazole-2-yl)-1,12-dihydroxy-1,2,3,4,5,6,7,8,10,13,14 -undecahydro-7,14,14,17-tetramethyl-1,10-methano-20H-cyclonona[2,3]benz[1,2-b]oxete;

4,9-Bis(acetyloxy)-2-benzoyloxy-8-(1,3-dithiolane-2-yl)-1,12-dihydroxy-1,2,3,4,5,6,7,8,10,13,14 -undecahydro-7,14,14,17-tetramethyl-1,10-methano-20H-cyclonona[2,3]benz[1,2-b]oxete;

(β-Benzoylamino-α-hydroxybenzenepropanoic acid 4,9-bis(acetyloxy)-2- benzoyloxy-1,2,3,4,5,6,7,8,10,13,14 -undecahydro-1-hydroxy-8-hydroxymethyl-7,14,14,17-tetramethyl-1,10-methano- 2OH-cyclonona[2,3]benz[1,2-b ]oxet-12-yl ester;

β-Benzoylamino-α-hydroxybenzenepropanoic acid 4,9-bis(acetyloxy)-2-benzoyloxy-1,2,3,4,5,6,7,8,10,13,14 -undecahydro-1-hydroxy-8-methoxymethyl-7,14,14,17-tetramethyl-1,10-methano- 2OH-cycionona[2,3]benz[1,2-b]oxet-12-yl ester;

β-Benzoylamino-α-hydroxybenzenepropanoic acid 4,9-bis(acetyloxy)-2-benzoyloxy-1,2,3,4,5,6,7,8,10,13,14 -undecahydro-1-hydroxy-8-ethoxymethyl-7,14,14,17-tetramethyl-1,10-methano- 2OH-cyclonona[2,3]benz[1,2-b ]oxet-12-yl ester;

β-Benzoylamino-α-hydroxybenzenepropanoic acid 4,9-bis(acetyloxy)-8-acetyloxymethyl-2-benzoyloxy- 1,2,3,4,5,6,7,8,10,13,14-undecahydro-1-hydroxy-7,14,14,17-tetramethyl-1,10-methano- 2OH-cyclonona[2,3]benz[1,2-b ]oxet-12-yl ester;

(β-Benzoylamino-α-hydroxybenzenepropanoic acid 4,9-bis(acetyloxy)-2-benzoyloxy- 8-dimethylaminomethyl-1,2,3,4,5,6,7,8,10,13,14-undecahydro-1-hydroxy-7,14,14,17-tetramethyl-1,10-methano-2OH-cyclonona[2,3]benz[1,2-b]oxet12-yl ester;

β-Benzoylamino-α-hydroxybenzenepropanoic acid 4,9-bis(acetyloxy)-2-benzoyloxy-8 -diethylaminomethyl-1,2,3,4,5,6,7,8,10,13,14-undecahydro-1-hydroxy-7,14,14,17 -tetramethyl-1,10-methano-2OH-cyclonona[2,3]benz[1,2-b]oxet12-yl ester;

1,3-Benzoylamino-α-hydroxybenzenepropanoic acid 4,9-bis(acetyloxy)-2-benzoyloxy-1,2,3,4,5,6,7,8,10,13,14 -undecahydro-1-hydroxy-7,14,14,17-tetramethyl-8-methylaminomethyl-1,10-methano-20 H-cyclonona[2,3]benz[1,2b]oxet-12-yl ester;

β-Benzoylamino-α-hydroxybenzenepropanoic acid 4,9-bis(acetyloxy)-2-benzoyloxy-1,2,3,4,5,6,7,8,10,13,14 -undecahydro-1-hydroxy-7,14,14,17-tetramethyl-8-methylimino-1,10-methano- 2OH-cyclonona[2,3]benz[1,2-b]oxet-12-yl ester;

β-Benzoylamino-α-hydroxybenzenepropanoic acid 4,9-bis(acetyloxy)-2-benzoyloxy-1,2,3,4,5,6,7,8,10,13,14 -undecahydro-1-hydroxy-7,14,14,17-tetramethyl-8-methoxyimino-1,10-methano- 2OH-cyclonona[2,3]benz[1,2-b]oxet-12yl ester;

β-Benzoylamino-α-hydroxybenzenepropanoic acid 4,9-bis(acetyloxy)-2-benzoyloxy-1,2,3,4,5,6,7,8,10,13,14 -undecahydro-1-hydroxy-7,14,14,17-tetramethyl-8-methyihydrazinomethyl-1,10-methano- 2OH-cyclonona[2,3]benz[1,2b]oxet-12-yl ester;

β-Benzoylamino-α-hydroxybenzenepropanoic acid 4,9-bis(acetyloxy)-2-benzoyloxy-8 -cyano-1,2,3,4,5,6,7,8,10,13,14-undecahydro-1-hydroxy-7,14,14,17-tetramethyl-1,10-methano- 2OH-cyclonona[2,3]benz[1,2-b]oxet-12-yl ester;

β-Benzoylamino-α-hydroxybenzenepropanoic acid 4,9-bis(acetyloxy)-2-benzoyloxy-8-( 1,3-dioxolane-2-yl)-1,2,3,4,5,6,7,8,10,13,14-undecahydro-1-hydroxy-7,14,14,17-tetramethyl-1,10-methano- 2OH-cyclonona[2,3]benz[1,2-b]oxet12-yl ester;

β-Benzoylamino-α-hydroxybenzenepropanoic acid 4,9-bis(acetyloxy)-2-benzoyloxy-8-(tetrahydro-oxazole- 2-yl)-1,2,3,4,5,6,7,8,10,13,14-undecahydro-1-hydroxy-7,14,14,17-tetramethyl- 1,10-methano-2OH-cyclonona[2,3]benz[1,2-b]o xet-12-yl ester;

β-Benzoylamino-α-hydroxybenzenepropanoic acid 4,9-bis(acetyloxy)-2-benzoyloxy-8-( 1,3-dithiolane-2-yi)-1,2,3,4,5,6,7,8,10,13,14-undecahydro-1-hydroxy-7,14,14,17-tetramethyl- 1,10-methano-2OH-cyclonona[2,3]benz[1,2-b]oxet12-yl ester;

(β-tert-Butyloxycarbonylamino-α-hydroxybenzenepropanoic acid 4,9-bis(acetyloxy)-2-benzoyloxy- 8- form yl-1,2,3,4,5,6,7,8,10,13,14-undecahydro-1- hydroxy- 7,14,14,17-tetramethyl-1,10-methano-2OH-cyclonona[2,3]benz[1,2-b]oxet12-yl ester;

β-tert-Butyloxycarbonylamino-α-hydroxybenzenepropanoic acid 4,9-bis(acetyloxy)-2-benzoyloxy-1,2,3,4,5,6,7,8,10,13,14 -undecah ydro-1-hydroxy-8-hydroxymethyl-7,14,14,17-tetramethyl-1,10-methano- 2OH-cyclonona[2,3]benz[1,2b]oxet-12-yl ester;

β-tert-Butyloxycarbonylamino-α-hydroxybenzenepropanoic acid 4,9-bis(acetyioxy)-2 -benzoyloxy-1,2,3,4,5,6,7,8,10,13,14-undecahydro-1-hydroxy-8-methoxymethyl-7,14,14,17-tetramethyl- 1,10-methano-2OH-cyclonona[2,3]benz[1,2b]oxet-12-yl ester;

β-tert-Butyloxycarbonylamino-α-hydroxybenzenepropanoic acid 4,9-bis(acetyloxy)-2-benzoyloxy- 1,2,3,4,5,6,7, 8, 10,13,14-undecahydro-1-hydroxy-8-ethoxymethyl-7,14, 14,17-tetramethyl- 1,10-methano-2OH-cyclonona[2,3]benz [1,2b]oxet-12-yl ester;

β-tert-Butyloxycarbonylamino-α-hydroxybenzenepropanoic acid 4,9-bis(acetyloxy)- 8-acetyloxymethyl-2-benzoyloxy-1,2,3,4,5,6,7,8,10,13,14-undecahydro-1-hydroxy-7,14,14,17-tetramethyl-1,10-methano-2OH-cyclonona[2,3]benz[1,2-b]oxet-12-yl ester;

β-tert-Butyloxycarbonylamino-α-hydroxybenzenepropanoic acid 4,9-bis(acetyloxy)-2-benzoyloxy- 8-dimethylaminomethyl-1,2,3,4,5,6,7,8,10,13,14-undecahydro-1-hydroxy- 7,14,14,17-tetramethyl-1,10-methano-2OH-cyclonona[2,3]benz[1,2-b]oxet-1 2-yl ester;

β-tert-Butyloxycarbonylamino-α-hydroxybenzenepropanoic acid 4,9-bis(acetyloxy)-2-benzoyloxy- 8-diethylaminomethyl-1,2,3,4,5,6,7,8,10,13,14-undecahydro-1-hydroxy-7,14,14,17-tetramethyl- 1,10-methano-2OH-cyclonona[2,3]benz[1,2-b]oxet-12-yl ester;

β-tert-Butyloxycarbonylamino-α-hydroxybenzenepropanoic acid 4,9-bis(acetyloxy)-2-benzoyloxy- 1,2,3,4,5,6,7, 8,10,13,14-undecahydro-1-hydroxy-7,14,14,17-tetramethyl-8-methylaminomethyl-1,10-methano- 2OH-cyclonona[2,3]benz[1,2-b]oxet-12-yl ester;

β-tert-Butyloxycarbonylamino-α-hydroxybenzenepropanoic acid 4,9-bis(acetyloxy)- 2-benzoyloxy-1,2,3,4,5,6,7, 8,10,13,14-undecahydro-1-hydroxy-7,14,14,17-tetramethyl- 8-methylimino-1,10-methano-2OH-cyclonona[2,3]benz[1,2b]oxet-12-yl ester;

β-tert-Butyloxycarbonylamino-α-hydroxybenzenepropanoic acid 4,9-bis(acetyloxy)-2-benzoyloxy- 1,2,3,4,5,6,7, 8,10,13,14-undecahydro-1-hydroxy-7,14,14,17-tetramethyl-8-methoxyimino- 1,10-methano-2OH-cyclonona[2,3]benz[1,2-b]oxet-12-yl ester;

β-tert-Butyloxycarbonylamino-α-hydroxybenzenepropanoic acid 4,9-bis(acetyloxy)-2-benzoyloxy- 1,2,3,4,5,6,7, 8,10,13,14-undecahydro-1-hydroxy-7,14,14,17-tetramethyl-8-methylhydrazinomethyl- 1,10-methano-2OH-cyclonona[2,3]benz[1,2-b]oxet-12-yl ester;

β-terttert-Butyloxycarbonylamino-α-hydroxybenzenepropanoic acid 4,9-bis(acetyloxy)-2-benzoyloxy- 8-cyano-1,2,3,4,5,6,7,8,10,13,14-undecahydro-1-hydroxy- 7,14, 14,17-tetramethyl-1,10-methano-2OH-cyclonona[2,3]benz [1,2-b]oxet12-yl ester;

β-tert-Butyloxycarbonylamino-α-hydroxybenzenepropanoic acid 4,9-bis(acetyloxy)-2-benzoyloxy- 8-(1,3-dioxolane-2-yl)-1,2,3,4,5,6,7,8,10,13,14-undecahydro-1-hydroxy- 7,14,14,17-tetramethyl-1,10-methano-2OH-cyclonona[2,3]benz[1,2-b]oxet-12-yl ester;

β-tert-Butyloxycarbonylamino-α-hydroxybenzenepropanoic acid 4,9-bis(acetyloxy)-2-benzoyloxy- 8-(tetrahydro-oxazole-2-yl)-1,2,3,4,5,6,7,8,10,13,14-undecahydro-1-hydroxy- 7,14,14,17-tetramethyl-1,10-methano-2OH-cyclonona[2,3]benz[1,2-b]oxet-12-yl ester;

β-tert-Butyloxycarbonylamino-α-hydroxybenzenepropanoic acid 4,9-bis(acetyloxy)- 2-benzoyloxy-8-(1,3-dithiolane-2-yl)-1,2,3,4,5,6,7,8,10,13,14-undecahydro-1-hydroxy- 7,14,14,17otetramethyl-1,10-methano-2OH-cyclonona[2,3]benz[1,2-b]oxet-12-yl ester;

β-Benzoylamino-α-hydroxy-γ-(1-naphthyl)propanoic acid 4,9-bis(acetyloxy)-2-benzoyloxy- 1,2,3,4,5,6,7,8,10, 13,14-undecahydro-1-hydroxy-8-hydroxymethyl-7,14,14, 17-tetramethyl- 1,10-meth ano-2OH-cyclonona[2,3]benz[1, 2-b ]oxet-12-yl ester; h β-Benzoylamino-α-hydroxy-γ-(2-naphthyl)propanoic acid 4,9-bis(acetyloxy)-2-benzoyloxy- 1,2,3,4,5,6,7,8,10, 13,14-undecahydro-1-hydroxy-8-hydroxymethyl-7,14,14, 17-tetramethyl- 1,10-methano-2OH-cyclonona[2,3]benz[1, 2-b ]oxet-12-yl ester;

β-Benzoylamino-α-hydroxy-γ-(pyridyl)propanoic acid 4,9-bis(acetyloxy)-2-benzoyloxy-1,2,3,4,5,6,7,8,10,13,14 -undecahydro-1-hydroxy-8-hydroxymethyl-7,14,14,17-tetramethyl-1,10-methano- 2OH-cyclonona[2,3]benz[1,2-b]oxet-12-yl ester;

β-tertBenzoylamino-α-hydroxy-γ-(thienyl)propanoic acid 4,9-bis(acetyloxy)-2-benzoyloxy-1,2,3,4,5,6,7,8,10,13, 14 -undecahyd ro-1-hydroxy-8-hydroxymethyl-7,14,14,17-tetramethyl-1,10-methano- 2OH-cyclonona[2,3]benz[1,2-b]oxet-12-yl ester;

β-Benzoylamino-α-hydroxy-γ-(furyl)propanoic acid 4,9-bis(acetyloxy)-2-benzoyloxyo 1,2,3,4,5,6,7,8,10,13,14-undecahydro-1-hydroxy-8-hydroxymethyl-7,14,14,17-tetramethyl- 1,10-methano-2OH-cyclonona[2,3]benz[1,2ob ]oxet-12-yl ester;

β-Benzoylamino-α-hydroxy-γ-(oxazolyl)propanoic acid 4,9-bis(acetyloxy)-2-benzoyloxy- 1,2,3,4,5,6,7,8,10,13,14-undecahydro-1-hydroxy-8-hydroxymethyl- 7,14,14,17-tetramethyl-1,10-methano-2OH-cyclonona[2,3]benz[1,2-b ]oxet-12-yl ester;

Iβ-Benzoylamino-α-hydroxy-γ-(imidazolyl)propanoic acid 4,9-bis(acetyloxy)-2-benzoyloxy- 1,2,3,4,5,6,7,8,10, 13,14-undecahydro-1-hydroxy-8-hydroxymethyl-7,14,14, 17-tetramethyl- 1,10-methano-2OH-cyclonona[2,3]benz[1, 2-b]oxet-12-yl ester;

(β-Benzoylamino-α-hydroxy-γ-(pyrazinyl)propanoic acid 4,9-bis(acetyloxy)-2-benzoyloxy-1,2,3,4,5,6,7,8,10,13, 14 -undecahydro-1-hydroxy-8-hydroxymethyl-7,14,14,17-tetramethyl-1,10-methano- 2OH-cyclonona[2,3]benz[1,2-b] oxet-12-yl ester; and β-Benzoylamino-α-hydroxy-γ-(pyridazinyl)propanoic acid 4,9-bis(acetyloxy)-2-benzoyloxy- 1,2,3,4,5,6,7,8,10, 13,14-undecahydro-1-hydroxy-8-hydroxymethyl-7,14,14, 17-tetramethyl-1,10-methano- 2OH-cyclonona[2,3]benz[1, 2-b ]oxet-12-yl ester, as well as their respective prodrugs.

Preferred among the compounds of the invention are 4,9,12-Tris(acetyloxy)- 2-benzoyloxy- 8-formyl-1,2,3,4,5,6, 7,8,10,13,14-undecahydro-1-hydroxy-7,14,14,17-tetramethyl-1,10-methano-2OH-cyclonona[ 2,3]benz[1,2-b]oxete; β-tert-Butyloxycarbonylamino-α-hydroxybenzenepropanoic acid 4,9-bis(acetyloxy)-2-benzoyloxy-8-formyl-1,2, 3,4,5,6,7,8,10,13,14-undecahydro- 1-hydroxy-7,14,14,17-tetramethyl-1,10-methano-2OH-cyclonona[2,3 ]benz[1,2-b] oxet-12-yl ester; and β-Benzoylamino-α-hydroxybenzenepropanoic acid 4,9-bis(acetyloxy)-2-benzoyloxy- 8-formyl-1,2,3,4,5,6,7,8, 10,13,14-undecahydro-1-hydroxy-7,14,14,17 -tetramethyl-1,10-methano-2OH-cyclonona[2,3]benz[1,2-b ]oxet-12-yl ester.

Of these, especially preferred and regarded as the best mode of carrying out the present invention is the compound β-tert-Butyloxycarbonylamino-echydroxybenzenepropanoic acid 4,9-bis(acetyloxy)-2-benzoyloxy-8-formyl-1,2, 3,4,5,6,7,8,10,13,14-undecahydro- 1-hydroxy-7,14,14,17-tetramethyl-1,10-methano-2OH-cyclonona[2,3]benz[1,2-b] oxet-12-yl ester.

The pharmaceutical compositions of the present invention comprise one or more of the above compounds in combination with a pharmaceutically acceptable carrier. By "pharmaceutically acceptable" is meant within the scope of sound medical judgement, suitable for use in contact with the tissues of humans and lower animals without undue toxicity, irritation, allergic response and the like, and are commensurate with a reasonable benefit/risk ratio. As used herein, the term "pharmaceutically acceptable carrier" means a non-toxic, inert solid, semi-solid or liquid filler, diluent, encapsulating material or formulation auxially of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatves and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The method of the present invention comprises treating tumors in a human or lower mammal by administering to a patient in need of such treatment a "therapeutically effective amount" of a compound of the invention, for such time as is necessary to achieve a therapeutic effect. By a "therapeutically effective amount" is meant a sufficient amount of the compound to treat a tumor, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.001 to 50 mg/kg body weight or more usually from 0.01 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

The process of the present invention involves the preparation of the above compounds of formula (11) from the compound of formula (I), which in turn is obtained by ring contraction of the B-ring of 9-dihydropaclitaxel or an appropriate 9dihydropaclitaxel derivative such as 9-dihydro-13-acetylbaccatin III (1). It has been found that compound 1 of the present invention may be obtained by alcoholic extraction from crushed needles and twigs of the Canadian yew, Taxus canadensis by the process disclosed in U.S. Pat. No. 5,352,806, issued Oct. 4, 1994, and incorporated herein by reference. This extract is then purified using customary separatory techniques, beginning with partitioning between solvent systems consisting of acetone, methanol, hexane, heptane and water to remove fats and lipids. The defatted crude extract is further partitioned, in several stages, between solvent systems consisting of methanol, methylene chloride, chloroform, ethyl acetate and water. Those fractions of the extract which are soluble in a solvent system consisting either of methylene chloride or of chloroform and ethyl acetate contain compound 1.

The above fractions may be further purified by planet coil countercurrent chromatography (PCCC), using solvent systems consisting of hexane, methanol, methylene chloride, chloroform, toluene, and water or suitable aqueous buffers. The various fractions contain several taxane derivatives, including paclitaxel, cephalomannine and baccatin III. The solvent is removed from the fraction containing compound 1, which is recrystallized from methanol or ethanol and water to afford the pure compound as white crystals. If desired, paclitaxel, baccatin, and other related compounds may also be isolated from the various chromatographic fractions.

Asymmetric centers may exist in the compounds of the present invention. The present invention contemplates the various stereoisomers and mixtures thereof. Starting compounds of particular stereochemistry are either commercially available or are made by the methods detailed below and resolved by techniques well known in the organic chemical arts.

In general, the compounds of formula (II) may then be synthesized from compound 1 by a rearrangement of the B-ring resulting in a ring-contracted product which is deprotected and then reacted with the appropriate side chain precursor. In one such process wherein Z is —CHO, illustrated below in Scheme 1, 13-acetyl-9-dihydrobaccatin III is dissolved in an inert solvent and treated with trifluoromethanesulfonic anhydride to give the desired ring-contracted compound 2. Compound 2 is treated with reagents such as butyllithium, methyllithium or lithium triethylborohydride to remove the acetyl group in the 12-position to give compound 3. Compound 3 may then be reacted with an appropriate protected side-chain derivative, (for example (2R,3S)-N-benzoyI-O-(1-ethoxyethyl)-3-phenylisoserine or (3R,4S)-N-benzoyl-3-O-(1-ethoxyethyl)-4-phenyl-2-azetidinone) and then removing the side-chain protecting group with mild acid to give compounds 6a or 6b, where R is benzoyl or an analogous moiety. Alternatively, 2'-O-(1-ethoxyethyl)- 9-dihydrotaxol (4) is prepared from compound 1 by omitting the ring-contraction step and proceeding as described above to remove the 13-acetyl group and then reacting the resulting hydroxy group with the appropriately protected side-chain. Compound 4 is then reacted with trifluorosulfonic anhydride Scheme 1
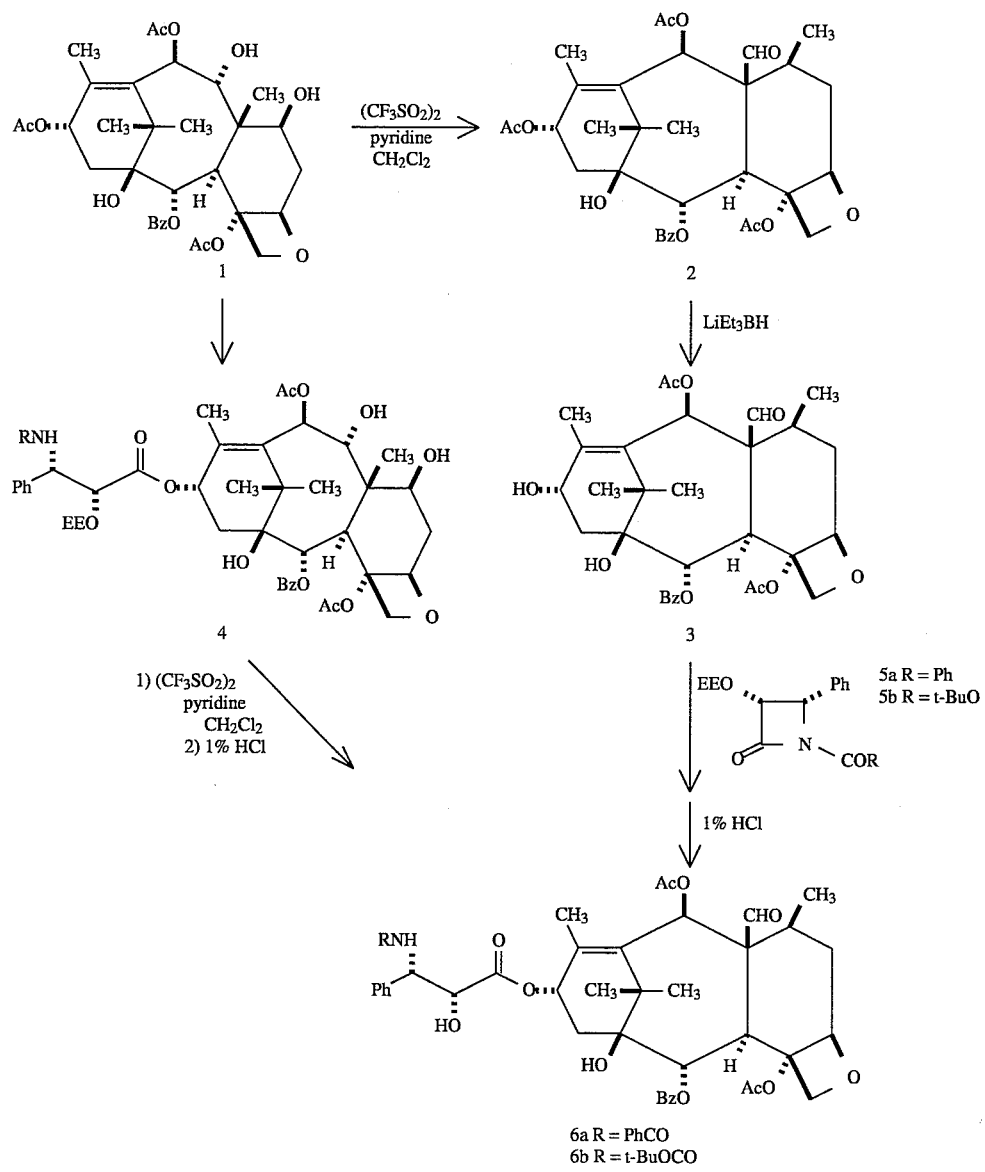

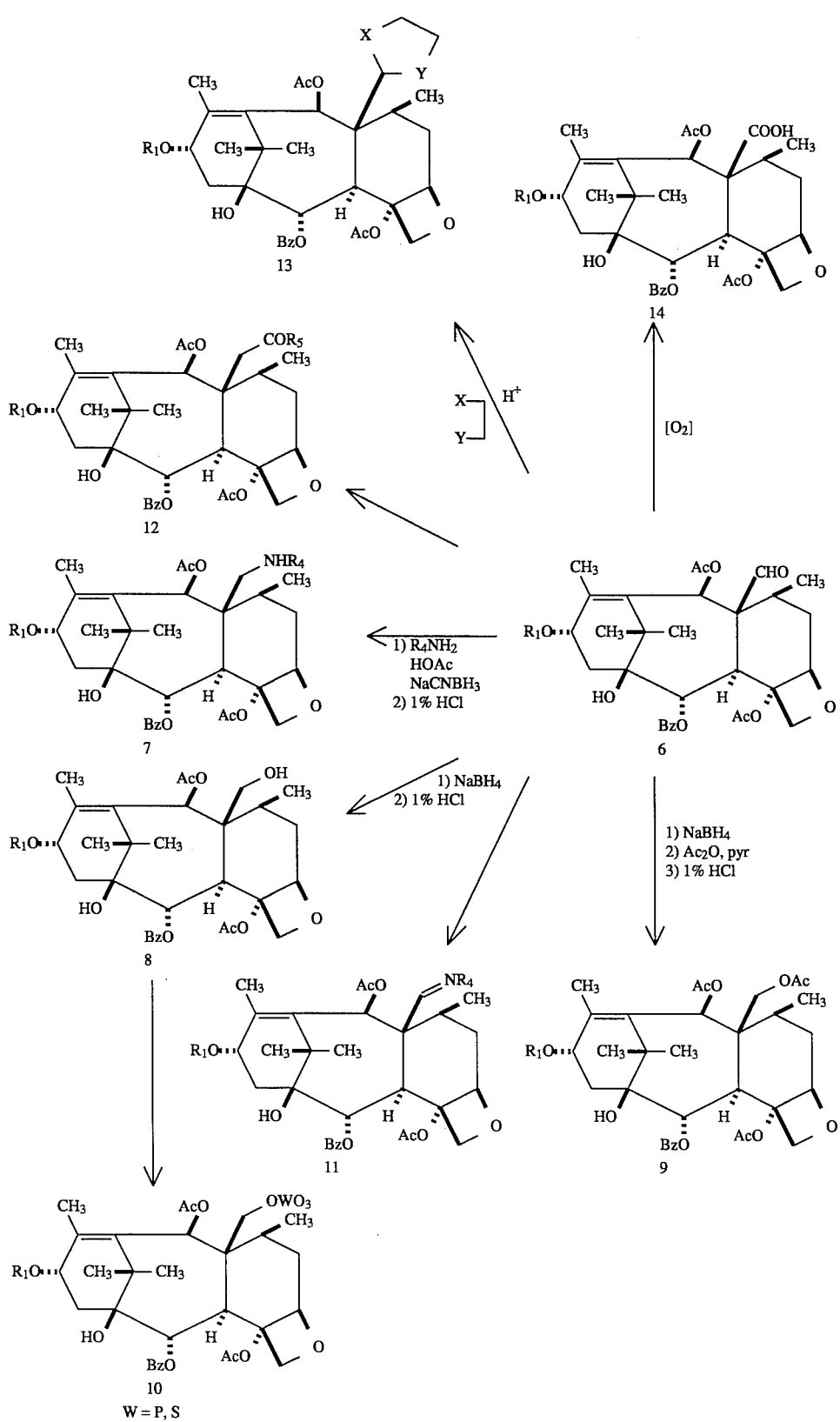
Scheme 2
in an inert solvent to give the ring-contracted rearrangement compound 6a or 6b directly.

The elaboration of the aldehyde functionality is described in Scheme 2. The aldehyde 6 can be reacted under reducing conditions with various amines followed by acid to give compound 7. Reduction with various reagents such as sodium borohydride produces hydroxymethyl compound 8, which can be alkylated to give alkoxymethyl compounds. Alternatively, reaction of the alcohol with phosphoryl or sulfuryl reagents leads to prodrugs 10 which are either phosphates or sulfates. Acetylation of the reduction product followed by deprotection gives compound 9. Treatment of 6 with various amine reagents under dehydrative conditions leads to imine, oxime and hydrazone derivatives 11. Simple oxidation of the aldehyde group leads to acid 14 which can be subsequently esterified, amidated and dehydrated to the corresponding nitrile. Homologation of the aldehyde via Wittig/Reformatsky technology leads to new functional chains at this position, as in for example compound 12. Mild acid treatment with reagents such as diols, dithiols, and aminoalcohols would lead to the formation of heterocycles such as those of compound 13 at the aldehyde position.

The foregoing may be better understood by reference to the following Examples, which are provided for purposes of illustration and not limitation of the invention. It will be appreciated by one skilled in the art that selective protection and deprotection steps affecting the several hydroxyl groups on the baccatin III structure may be carried out in varying order or number of steps, as necessary, and that Schemes 1 and 2 are intended to encompass such variations. Also, it will noted that the following abbreviations are used in describing some of the particular reagents and conditions utilized in the above syntheses: $CH_2Cl_2$ for methylene chloride, EtOAc for ethyl acetate, LiHMDS for lithium hexamethyldisilazide and THF for tetrahydrofuran.

EXAMPLE 1

4.9.12-Tris(acetyloxy)-2-benzoyloxy-8-formyl-1,2,3,4.5.6.7.8.10.1-undecahydro-1-hydroxy-7.14.14.17 -tetramethyl-1,10-methano-20H-cyclonona[2.3]benz[1,2-b]oxete (Scheme 1, Compound (2))

To 25 mg of 13-acetyl-9-dihydrobaccatin III (1) dissolved in $CH_2Cl_2$ (1 mL) and pyridine (0.064 mL, 20 eq.) at 0 ° C. under nitrogen was added a 10% solution of trifluoromethanesulfonic anhydride in $CH_2Cl_2$ dropwise with stirring until an orange color persisted. After 1 hour the reaction was complete by thin layer chromatographic analysis. The reaction was quenched by the addition of pH 7 phosphate buffer and the organic layer was separated, dried, and evaporated in vacuo. The residue was purified by silica gel column chromatography eluting with 1:1 ethyl acetate-hexane to give 13.6 mg of the title compound. $^1H$ NMR ($CDCl_3$, 300 MHz) ,5 10.24 (d, 1H, CHO), 8.18 (d, 2H, ArH), 7.61 (t, 1H, ArH), 7.5 (t, 2H, ArH), 6.28 (s, 1H, H-10), 6.07 (t, 1H, H-13), 5.83 (d, 1H, H-2), 5.21 (d, 1H, H- $20_a$), 4.9 (dd, 1H, H-5), 4.19 (d, 1H, H-$20_b$) , 2.45 - 2.44 (m, 1H, H-7), 2.48 (d, 1H, H-3 OAc), 2.2 (s, 3H, OAc), 2.23-2.1 (m, 2H, H-$6_a$, H-$14_a$), 2.18 (s, 3H, OAc), 2.0 (dd, H-$14_b$), 1.94 (d, 3H, vinyl-$CH_3$), 1.62 (ddd, 1 H, H-$6_b$), 1.22 (d, 3H, C7-$CH_3$), 3H, $CH_3$), 1.1 (s, 3H, $CH_3$). MS (DCI/$NH_3$) m/e 613 (M+H)$^+$, 630 (M+H+$NH_3$)$^+$. Recrystallized from 1:1 MeOH-water for x-ray structure.

Single crystal X-ray diffraction analysis: Source, Cu Kα; symmetry, monoclinic; unit cell constants, a=15.935 (3), b=12.749 (1), c=15.902 (2) Å, β=97.746 (9)° as determined from 25 diffractometer-measured 2θ values; systematic extinctions and density considerations uniquely consistent with space group P2$_1$ with two molecules of composition $C_{33}H_{40}O_{11}$ per asymmetric unit; total reflections, 5196; solution obtained by direct methods, with structure illustrated in FIG. 1; in final model, non-hydrogen atoms anisotropic, discrepancy index R= 0.045.

EXAMPLE 2

4.9-Bis(acetyloxy)-2-benzoyloxy-8-formyl-1.2.3.4.5.6.7.8.10.13,14-undecahydro-1.12-dihydroxy-7.14.14.17-tetramethyl-1.10-methano-20H-cycleno.na[2,3]benz-[1.2-b]oxete (Scheme 1. Compound (3))

To a solution of the compound resulting from Example 1 (27 mg) in THF (5 mL) stirred at $-78$ ° C. under nitrogen was added Super Hydride (LiEt $_3$BH, 1 M in THF, 0.128 mL) dropwise. After ten minutes the reaction was complete by thin layer chromatographic analysis. The reaction was quenched by the addition of pH 7 phosphate buffer and $CH_2Cl_2$, and the organic layer was separated, dried, and evaporated in vacuo. The residue was purified by silica gel column chromatography eluting with 95:5 $CH_2Cl_2$-MeOH to give 18 mg of the title compound. $^1H$ NMR ($CDCl_3$, 300 MHz)δ 10.28 (d, 1H, CHO), 8.18 (d, 2H, ArH), 7.6 (t, 1H, ArH), 7.48 (t, 2H, ArH), 6.28 (s, 1H, H-10), 5.79 (d, 1H, H-2), 5.21 (d, 1H-$20_a$), 4.9 (dd, 1H, H-5), 4.86 (t, 1H, H-13), 4.18 (d, 1H, H-$20_b$ ), 2.51 (d, 1H, H-3), 2.5- 2.4 (m, 1H, H-7), 2.25 (s, 3H, OAc), 2.19 (s, 3H, OAc), 2.25 -2.0 (m, 3H, H-$6_a$, H-$14_{a,b}$), 2.09 (d, 3H, vinyl-$CH_3$), 1.62 (ddd, 1H, H-$6_d$), 1.23 (d, 3H, C7-$CH_3$), 1.1 (s, 3H, $CH_3$) 1.0 (s, 3H, $CH_3$). MS (DCI/$NH_3$) m/e 588 M+H+$NH_3$)$^+$.

EXAMPLE 3

8-tert-Butyloxycarbonylamino-α-hydroxybenzenepropanoic acid 4,9-bis(acetyloxy)-2-benzoyloxy-8-formyl-1.2.3.4.5.6.7.8.10.13.14-undecahydro-1-hydroxy-7.14.14.17-tetramethyl-1.10-methano- 20H-cyclonona[2.3]benz[1.2.b]oxet-12-yl ester (Scheme 1, Compound (6b))

To a solution of the compound resulting from Example 2 (18 mg) in THF (2 mL) stirred under nitrogen at $-78$ ° C. was added LiHMDS (1M in THF, 0.063 mL, 2 eq.) dropwise and after 15 minutes lactam 5b ((3R,4S)-N-tert-butyloxycarbonyl-3-O-(1-ethoxyethyl)- 4-phenyl-2-azetidinone) was added in THF (1 mL, 2 eq.). The cooling bath was changed to ice and after 15 minutes the reaction was complete by thin layer chromatographic analysis. The reaction was quenched by the addition of pH 7 phosphate buffer and $CH_2Cl_2$, and the organic layer was separated, dried, and evaporated in vacuo The residue was treated with 1% HCl in ethanol (2 mL) and stirred at 25 ° C. for four hours at which time the reaction was complete by thin layer chromatographic analysis. The reaction was quenched by the addition of pH 7 phosphate buffer and concentrated in vacuo before partitioning between water and $CH_2Cl_2$. The organic layer was separated, dried and evaporated in vacuo, and the residue was purified by silica gel column chromatography eluting with 95:5 $CH_2Cl_2$-MeOH to give 13 mg of the title compound. 1H NMR ($CDCl_3$) δ 10.24 (d, 1H, OHO), 8.23 (d, 2H, ArH), 7.6-7.3 (m, 14H, ArH, NH), 6.3 (s, 1H, H-10), 6.3 (t, 1H, H-13), 5.9 (d, 1H, H-2), 5.85 (br d, 1H, H-3'), 5.18 (d, 1H, H-20)$_,$ 4.83 (dd 4.62 (br s, 1H, H-2'), 4.15 (d, 1H, H-$20_b$), 3.15 (d, 1H, C3-OH), 2.55 (d, 1H, H-3), 2.35 -2.5 (m, 1H, H-7_), 2.38 (s, 3H, OAc), 2.2 (s, 3H, OAc), 2.2-2.1 (m, 3 H, H-$6_a$, H-$14_{a,b}$), 1.91 (br s, 3H, vinyl-$CH_3$), 1.65 (ddd, 1H, H-$6_b$), 1.27 (d, 3H, C7-$CH_3$), 1.2 (s, 9H, t-Bu), 1.16 (s, 3H, CH₃), 1.14 (s, 3H, CH₃).

EXAMPLE 4

β-Benzoylamino-α-hydroxybenzenepropanoic acid 4,9-bis(acetyloxy)-2-benzoyloxy-8-formyl-1.2.3.4.5.6.7.8.10.13.14-undecahydro-1-hydroxy-7.14.14.17-tetramethyl-1.10-m,ethano-20H-cyclonona[2.3]benz[1.2-b]oxet -12-yl ester (Scheme 1, Compound (6a))

2'-Ethoxyethyl-9-dihydropaclitaxel (4) (10 mg) was treated by the procedure described in Example 1 to give the corresponding rearranged product. After a workup as described in Example 1, the crude product was treated with 1% HCl in EtOH for four hours at 25° C. and then quenched with buffer and CH₂Cl₂. The combined organic extracts were washed, dried and concentrated in vacuo to afford a residue which was purified by silica gel column chromatography eluting with 95:5 CH₂Cl₂-MeOH to give 1.8 mg of the title compound. ¹H NMR (CDCl₃, 300 MHz) δ 10.25 (d, 1H, CHO), 8.26 (d, 2H, ArH), 7.7-7.3 (m, 13H, ArH), 6.99 (d, 1H, NH), 6.3 (s, 1H, H-10), 6.22 (t, 1H, H-13), 5.92 (d, 1H, H-2), 5.85 (br d, 1H, H-3'), 5.2 (d, 1H H-20$_a$), (4.83 (dd, 1H, H-5) 4.78 (br s, 1H, H-2'), 4.17 (d, 1H, H-20$_b$) 3.3 (d, 1H, C3-OH), 2.59 (d, 1H, H-3), 2.5 (m, 1H, H-7), 2.4 (s, 3H, OAc), 2.26 (dd, 1H, H-14 $_a$), 2.2 (s, 3H, OAc), 2.25-2.0 (m, 2H, H-6$_a$), H-14$_b$), 1.92 (br s, 3H, vinyl-CH₃), 1.62 (ddd, 1H, H-6$_a$), 1./29 (d, 3H, C7-CH₃), 1.2 (s, 3H, CH₃).

EXAMPLE 5

Assay for In Vitro Tumor Cell Cytotoxicity

The compounds of the present invention were tested for in vitro cytotoxic activity against the tumor lines A549 (human breast cancer), HT-29 (human lung cancer), B16F10 (mouse melanoma) and P-388 (mouse leukemia). Concentrations of 50% growth inhibition (IC$_{50}$'s) were measured in a colorimetric assay for cytotoxic activity against cultured cells according to the protocol described below:

A three-day microtiter assay was used to measure the growth inhibition of cultured cells exposed to a range of drug concentrations. Metabolic activity, and thus the continued survival of cells exposed to the test compounds, was measured by the cells' ability to reduce the tetrazolium dye, MTT (3-(4,5-dimethyl-thiazol-2-yl-2,5-diphenyltetrazolium bromide) to a quantifiable colored end product, which absorbs at 570 nm in the visible spectrum.

Test compounds were dissolved in dimethyl sulfoxide (DMSO) and diluted, first with Earle's Balanced Salt Solution followed by culture medium, to twice the highest concentration of compound to be tested. From this concentrated stock, twofold serial dilutions were prepared in 96-well microtiter trays, each well containing twice the desired final concentration of compound. Each concentration was tested in triplicate and compared to triplicate drug-free controls.

The cells were grown in the same medium used for diluting the compounds and then harvested using trypsinization. This involved removing the medium by aspiration; rinsing the cell monolayer twice with Earle's Balanced Salt Solution; adding trypsin (0.05%)/EDTA (0.53 mM; for each 25 cm², approximately 0.2 mL), tilting to cover the monolayer, and then withdrawing trypsin leaving only a thin film of solution; incubating at room temperature until the cell monolayers detached (as determined by visual and/or microscopic observation); adding medium containing fetal calf serum to stop the action of the trypsin and resuspend the cells; triturating to aid dissociation of cell clumps; and determining the number of cells per milliliter by electronic cell counter (e.g. Coulter Counter) or by mixing an aliquot of cell suspension with Trypan Blue (0.4% in normal saline) and counting the viable cells using a hemacytometer.

After harvesting and determination of viable cell counts, cell density was adjusted to 25,000 cells/mL. Inoculum (0.1 mL) containing the cells was then added to each well for a final concentration of 2,500 cells per well. Addition of the inoculum diluted the test compounds to the desired final concentration.

Microtiter trays were then incubated for three days at 36° C. in a humidified atmosphere containing 5% carbon dioxide. After three days, 20 microtiters of 5 mg/mL MTT in phosphate-buffered saline solution were added to each well. Trays were returned to the incubator for two to four hours to allow the surviving cells to reduce the dye. Medium and unreduced dye were removed by aspiration. DMSO was added to each well to dissolve the water-insoluble, colored end product of the dye reduction so that it could be measured spectrophotometrically at 570 nm. The IC$_{50}$ was determined as the concentration of compound tested required to reduce the absorbance at 570 nm to 50% of non-drug treated control values.

The results of testing, shown in Table 1, below, demonstrate the cytotoxic activity of the compounds of the present invention.

TABLE 1

| | In Vitro Tumor Cell Cytotoxicity (IC$_{50}$'s in µg/mL) | | | |
|---|---|---|---|---|
| Sample | A549 | HT-29 | B16F10 | P388 |
| Example 3 | 0.0098 | 0.0054 | 0.0046 | 0.0083 |
| Example 4 | 0.017 | 0.076 | 0.045 | 0.032 |
| Paclitaxol | 0.0034 | 0.0025 | 0.0031 | 0.0096 |

It is understood that the foregoing detailed description and accompanying examples are merely illustrative and are not to be taken as limitations upon the scope of the invention, which is defined solely by the appended claims and their equivalents. Various changes and modifications to the disclosed embodiments, which will be apparent to those skilled in the art, may be made without departing from the spirit and scope of the present invention.

What is claimed is:

1. A compound or prodrug thereof having the formula

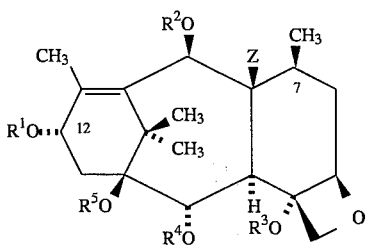

or a prodrug thereof, wherein

R¹ is selected from the group of hydrogen, alkanoyl and a radical having the formula

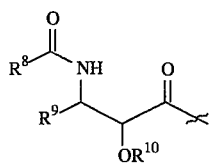

in which $R^8$ is selected from the group consisting of hydrogen, alkyl, phenyl, substituted phenyl, alkoxy, substituted alkoxy, amino, substituted amino, phenoxy and substituted phenoxy; $R^9$ is selected from the group consisting of hydrogen, alkyl, hydroxyalkyl, alkoxyalkyl, aminoalkyl, phenyl and substituted phenyl; and $R^{10}$ is selected from the group consisting of hydrogen, alkanoyl, substituted alkanoyl and aminoalkanoyl;

$R^2$ and $R^3$ are acetyl;

$R^4$ is phenylcarbonyl;

$R^5$ is hydrogen; and

Z is —CHO.

2. A compound according to claim 1 wherein $R^1$ is a radical having a formula selected from the group consisting of

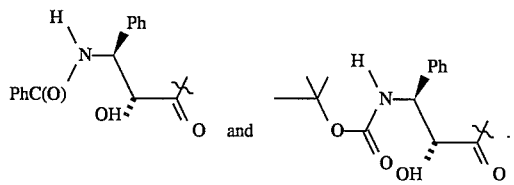

3. A compound according to claim 1 wherein $R^1$ is acetyl.

4. A compound according to claim 1 selected from the group consisting of 4,9,12-Tris(acetyloxy)-2-benzoyloxy-8-formyl-1,2,3,4,5,6,7,8,10,13,14-undecahydro-1-hydroxy- 7,14,14,17-tetramethyl-1,10-methano-20H-cyclonona[2,3]benz[1,2-b]oxete;

β-tert-Butyloxycarbonylamino-α-hydroxybenzenepropanoic acid 4,9-bis(acetyloxy)-2-benzoyloxy-8-formyl- 1,2,3,4,5,6,7,8,10,13,14-undecahydro-1-hydroxy-7,14,14,17-tetramethyl-1,10-methano- 20H-cyclonona[2,3]benz[1,2-b]oxet-12-yl ester; and β-Benzoylamino-α-hydroxybenzenepropanoic acid 4,9-bis(acetyloxy)-2-benzoyloxy-8-formyl- 1,2,3,4,5,6,7,8,10,13,14-undecahydro-1-hydroxy-7,14,14,17-tetramethyl-1,10-methano- 20H-cyclonona[2,3]benz[1,2-b]oxet-12-yl ester, or a prodrug thereof.

5. A pharmaceutical composition comprising a pharmaceutically acceptable carrier and a compound according to claim 1.

6. A pharmaceutical composition comprising a pharmaceutically acceptable carrier and a compound according to claim 1.

7. A method for inhibiting tumors in a mammal in need of such treatment, comprising administering to the mammal a therapeutically effective amount of a compound of claim 1.

8. A method for inhibiting tumors in a mammal in need of such treatment, comprising administering to the mammal a therapeutically effective amount of a compound of claim 4.

* * * * *

UNITED STATES PATENT AND TRADEMARK OFFICE
CERTIFICATE OF CORRECTION

PATENT NO. : 5,468,769
DATED : November 21, 1995
INVENTOR(S) : Larry L. Klein, et al.

It is certified that error appears in the above-indentified patent and that said Letters Patent is hereby corrected as shown below:

Column 22, Line 52, delete

--or prodrug thereof--.

Signed and Sealed this

Twenty-ninth Day of October 1996

BRUCE LEHMAN

*Attest:*

*Attesting Officer*     *Commissioner of Patents and Trademarks*